Nov. 25, 1969 | I. F. MACKAY | Plant Pat. 2,942
ROSE PLANT
Filed March 11, 1968
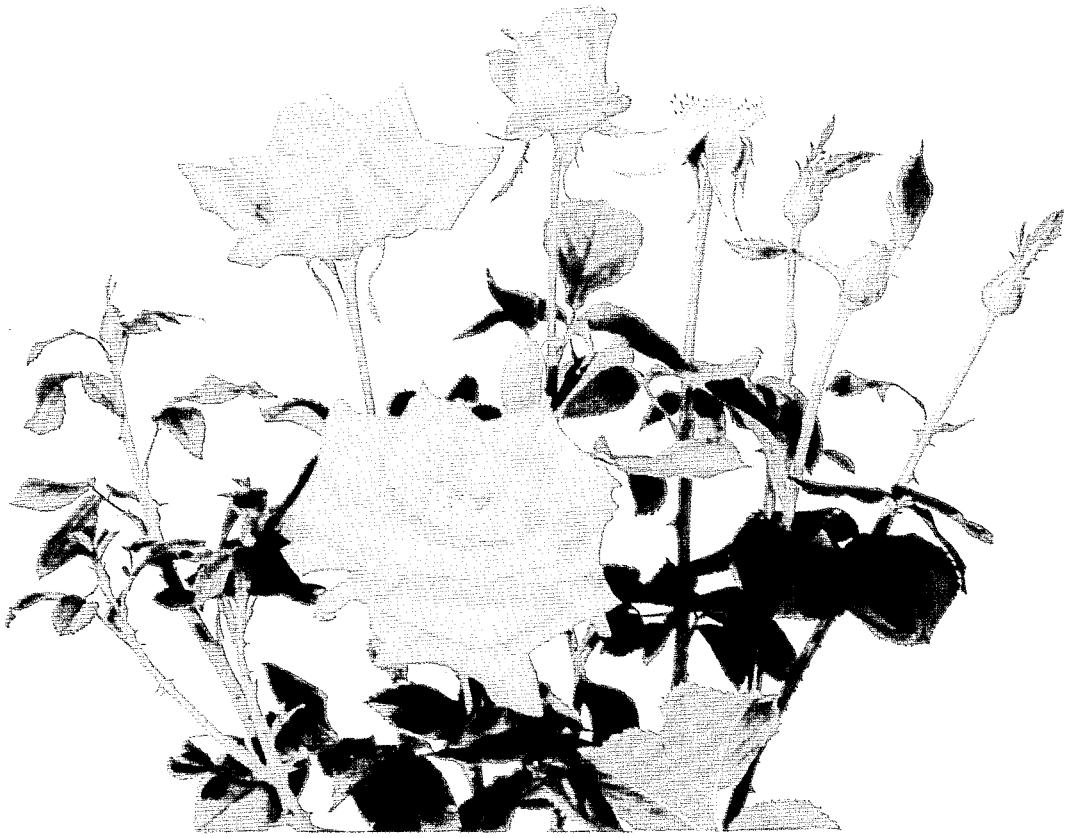
Ian F. Mackay
By
Berman, Doane, Benedict, Summerhes & Martin
Attorneys

United States Patent Office

Plant Pat. 2,942
Patented Nov. 25, 1969

2,942
ROSE PLANT

Ian F. Mackay, St. Charles, Ill., assignor, by mesne assignments, to Texas Rose Research Foundation, Inc., Tyler, Tex., a corporation of Texas Filed Mar. 11, 1968, Ser. No. 712,309
Int. Cl. A01h 5/02
U.S. Cl. Plt.—20 1 Claim

ABSTRACT OF THE DISCLOSURE

A new and distinct variety of hybrid tea rose plant produced by crossing President Eisenhower, Plant Patent No. 1,217, on Suspense, Plant Patent No. 1,944.

The present invention relates to a new and distinct variety of rose plant of the hybrid tea class which was originated by crossing President Eisenhower (Plant Patent 1,217) on Suspense (Plant Patent No. 1,944).

This rose differs from its seed parent President Eisenhower (Plant Patent No. 1,217) by being a taller, more vigorous and freely branched plant with more abundant bloom of a much darker color.

This rose differs from its pollen parent Suspense (Plant Patent No. 1,944) by having a more freely branched plant habit and greater production of bloom which is of essentially solid color somewhat less brilliant than the red of the inner petal surface of the pollen parent.

The accompanying drawing shows typical specimens of the growth and habit of my new variety in different stages of development and in a color as nearly true as is possible to make the same in a color illustration of this character.

The following is a detailed description of my new rose variety with color terminology in accordance with the Horticultural Color Chart of the Royal Horticultural Society, except where general color terms of ordinary dictionary significance are used:

Type: Hardy; bush; seedling; for garden decoration.
Class: Hybrid tea.

*The flower*

Locality where grown: West Grove, Pa.
Flowers borne: Usually singly, occasionally three to stem; in irregular cluster; on normal, medium stems.
Quantity of bloom: Free, outdoors.
Continuity: Continuous.
Fragrance: Slight; centifolia.

Bud:
- *Peduncle.*—Medium length; slender to medium heavy; medium strength; light green, almost smooth; few hairs; red brown.
- *Before calyx breaks.*—Size: Medium. Form: Medium pointed with a conspicuous neck; with foliaceous appendages on the surface of the bud; with slender medium-cut foliaceous parts extending beyond the tip of the bud equal to ½ or more of its length.
- *As calyx breaks.*—Color: Indian Lake 826.
- *As first petal opens.*—Size: Medium. Form: Medium pointed. Color: Outside.—Indian Lake 826; Sulphur Yellow 1 at point of attachment. Inside.—Currant Red 821 overlaid with velvet tones of Maroon 1030; Sulphur Yellow 1 at point of attachment.
- *Opening.*—It does open up well.

Bloom:
- *Size when fully open.*—Medium, 3½ inches to 4½ inches.
- *Petalage.*—Double; from 30 to 40 petals; arranged regularly.

- *Form.*—High centered at first; becoming flat; petals remaining at first loosely rolled outward; becoming later at maturity loosely rolled outward.

Petals: Medium soft; with inside velvety; outside satiny.
- *Shape.*—Outer: Round; usually with 1 notch. Intermediate: Obovate; with 2 teeth. Inner: Round to obovoate; irregular; with 1 notch.
- *Color.*—Colors may be modified by being shaded with other colors.

This description of a newly opened flower was made from a rose grown outdoors in July, 1967, at West Grove, Pa.

- *Color.* — Outer petal: Outside surface.—824/1 Chrysanthemum Crimson; Sulphur 1 at point of attachment. Inside surface.—824 Chrysanthemum Crimson with velvet tones of Maroon 1030; Sulphur 1 at point of attachment. Intermediate petal.—Outside surface: Tyrian Purple 727. Sulphur Yellow 1 at point of attachment; inside surface: Brighter than Currant Red 821; Sulphur 1 at point of attachment. Inner petal: Outside surface.—Cardinal Red 822/3; Sulphur Yellow 1 at point of attachment. Inside surface.—Deeper than Cardinal Red 822; Sulphur Yellow 1 at point of attachment.

This description was made from a rose that was open for three days, outdoors in July 1967 at West Grove, Pa.

- *Color.*—Outer petal: Outside surface.—Cardinal Red 822/2; Sulphur 1 at point of attachment. Inside surface.—Deeper than Currant Red 221; Sulphur 1 at point of attachment. Inner petal: Outside surface.—Rose Opal 022; Sulphur Yellow 1 at point of attachment. Inside surface: Currant Red 821; Sulphur Yellow 1 at point of attachment.
- *General color effect.*—Newly opened flower: Brighter than Cardinal Red 822. Three days open: Near Currant Red 821.
- *Behavior.*—Drop off cleanly.
- *Flower longevity.*—On bush in garden 5 days in July; cut roses kept at living room temperatures 4 days in July.

*Reproductive organs*

Stamens: Medium; arranged regularly about pistils, occasionally mixed with petaloids.
Filaments: Many; with anthers; long.
- *Color.*—Yellow to pink (general color terms).

Anthers.—All open at once.
- *Color.*—Maroon (general color terms). Seldom an anther fused with a pistil.

Pollen: Moderate; gold.
Pistils: Medium.
Styles: Uneven; short; thin; loosely bunched.
Stigma: White purple.
Ovaries: all enclosed in receptacle.
Hips: None observed.
Sepals: Falling soon.
Seeds: None observed.

*Plant*

Foliage:
- *Leaves.*—Compound of 5 leaflets; abundant, medium size; moderately heavy somewhat glossy.
- *Leaflets.*—Shape: Oval with apex acute; base obtuse, doubly dentate.
- *Color.* — Mature: Upper surface.—Leek Green 000868; under surface.—Leek Green 000858/1; Young: Upper surface.—Near Dahlia Purple 931; under surface.—Near Garnet Lake 828.

*Rachis (the supporting stem of the compound leaf)*.—Light. Upper side: Hairy. Under side: Moderately prickly.

*Stipules*.—Short; narrow; with short points; turning out at an angle of less than 90°;

*Disease*.—Resistance comparable to the average variety growing under the same cultural conditions.

Growth:

*Habit*.—Upright, much branched.

*Growth*.—Free.

*Canes*.—Medium to heavy.

*Main Stems*. Dull.—Color: Willow Green 000862.

*Prickles*. Many.—Color: Maroon (general color term).

*Hairs*. Many—Color: Maroon (general color term) glandular tipped.

*Branches*. Dull.—Color: Willow Green 000862/1 sometimes overlaid with maroon (general color term). Prickles: Many.—Color: Maroon (general color term).

*Hairs*. Several.—Color: Maroon (general color term) glandular tipped.

*New shoots*. Dull.—Color: Near Scheeles Green 860.

*Prickles*. Several.—Color: Pea Green 61/1.

*Hairs*. Several.—Color: Maroon (general color term) glandular tipped.

I claim:

A new and distinct variety of rose plant in the hybrid tea class, substantially as herein shown and described, characterized by the deep velvety red color of the bud opening to a bright cardinal red double bloom lasting well on the bush or when cut, borne singly and occasionally two or three on medium long stems continuously through the season and with slight centifolia fragrance, and characterized by free growth of upright and much branched habit with medium to heavy canes abundantly covered with moderately heavy, somewhat glossy foliage with disease resistance comparable to the average variety.

No references cited.

ROBERT E. BAGWILL, Primary Examiner